United States Patent [19]

Horgan et al.

[11] 4,069,222

[45] Jan. 17, 1978

[54] PROCESS FOR PREPARING 2-(2,2-DICYCLOHEXYLETHYL)PIPERIDINE

[75] Inventors: Stephen W. Horgan; Frank P. Palopoli, both of Montgomery, Ohio; Edward J. Schwoegler, Munster, Ind.

[73] Assignee: Richardson-Merrell Inc., Wilton, Conn.

[21] Appl. No.: 677,069

[22] Filed: Apr. 14, 1976

[51] Int. Cl.$^2$ ............................................ C07D 211/10
[52] U.S. Cl. ................................. 260/293.52; 424/267
[58] Field of Search .................... 260/293.52; 252/477

[56] References Cited

U.S. PATENT DOCUMENTS 2,813,100  11/1957  Levy ................................. 260/293.2

FOREIGN PATENT DOCUMENTS 641,026  8/1950  United Kingdom ............ 260/293.52

*Primary Examiner*—Cecilia M. S. Jaisle
*Attorney, Agent, or Firm*—William J. Stein; Eugene O. Retter; George W. Rauchfuss, Jr.

[57] ABSTRACT

2-(2,2-Dicyclohexylethyl)piperidine is prepared via the catalytic hydrogenation of 2-(2,2-diphenylethenyl)pyridine in a single step. High yields are obtained using an anhydrous Raney nickel catalyst.

5 Claims, No Drawings

PROCESS FOR PREPARING 2-(2,2-DICYCLOHEXYLETHYL)PIPERIDINE

BACKGROUND OF THE INVENTION

The compound 2-(2,2-dicyclohexylethyl)piperidine, known by its generic name perhexiline, is a well-established chemical entity. In the form of its maleate salt it is used for the prevention of angina pectoris in patients with coronary artery disease. Perhexiline maleate can be represented by the following chemical structural formula:

In the past, perhexiline (I) has been prepared by reacting α-picoline (II) with phenyl-lithium to form α-picolyl-lithium. The α-picolyl-lithium is not isolated but condensed with dicyclohexyl ketone (III) to form α,α-dicyclohexyl-2-pyridineethanol (IV). Dehydration of the pyridineethanol using a conventional dehydrating agent, such as phosphoric acid (85%), alcoholic hydrogen chloride or hydrogen bromide results in the preparation of 2-(2,2-dicyclohexylethenyl)pyridine (V), as shown in U.S. Pat. No. 3,038,905. Hydrogenation of the pyridine ring and the double bond to form perhexiline is accomplished using low pressure hydrogen (4 atmospheres) in the presence of a platinum oxide catalyst, as disclosed in British Pat. No. 1,025,578. This reaction sequence can be depicted as follows:

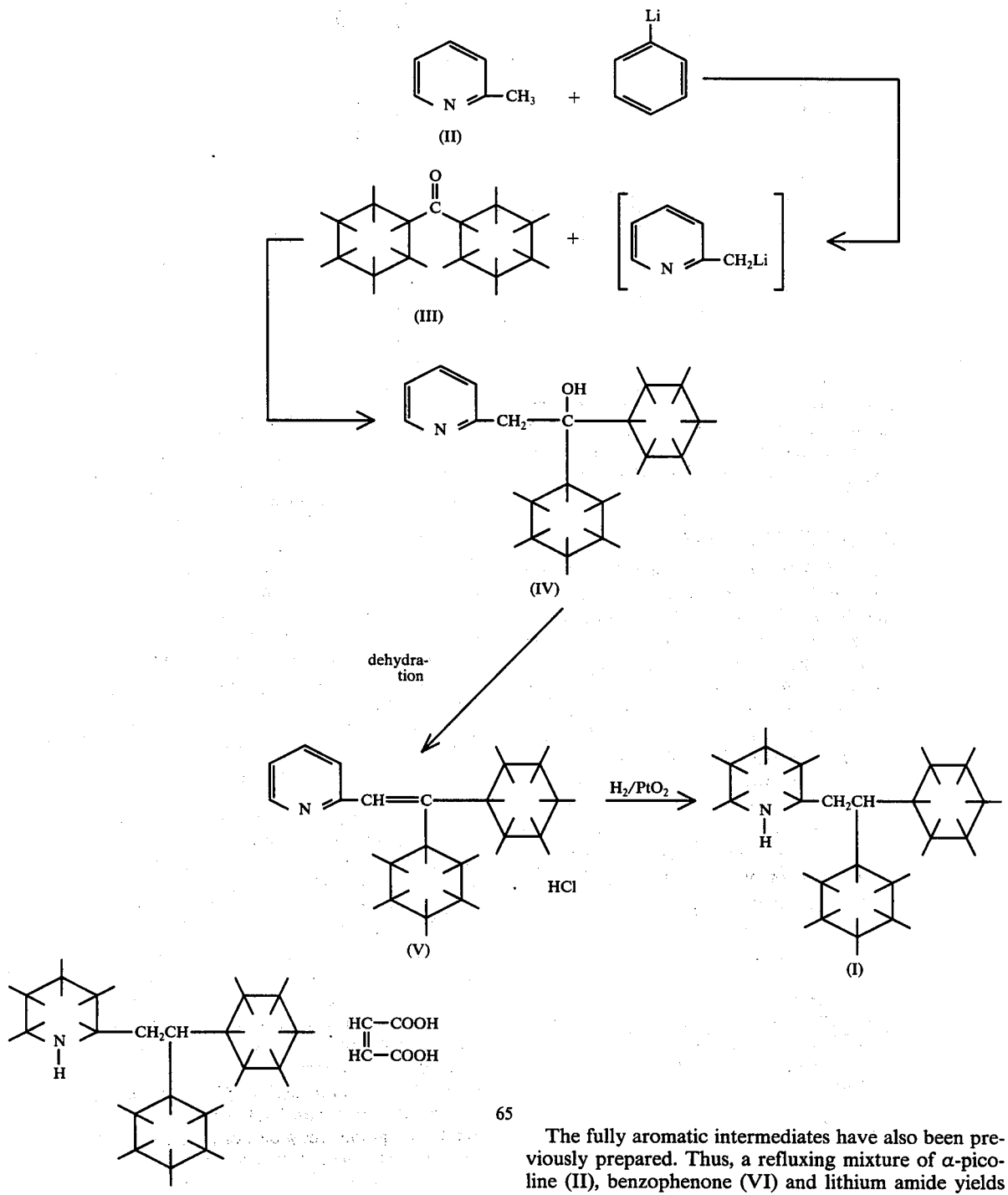

The fully aromatic intermediates have also been previously prepared. Thus, a refluxing mixture of α-picoline (II), benzophenone (VI) and lithium amide yields α,α-diphenyl-2-pyridineethanol (VII) in accordance with the procedure set forth by Tilford et al., J. Am. Chem. Soc. 76, 2431, 2434 (1954). Dehydration of the pyridineethanol with dilute hydrochloric acid or 48 percent HBr results in the preparation of 2-(2,2-diphenylethenyl)pyridine (VIII). This reaction sequence can be indicated as follows:

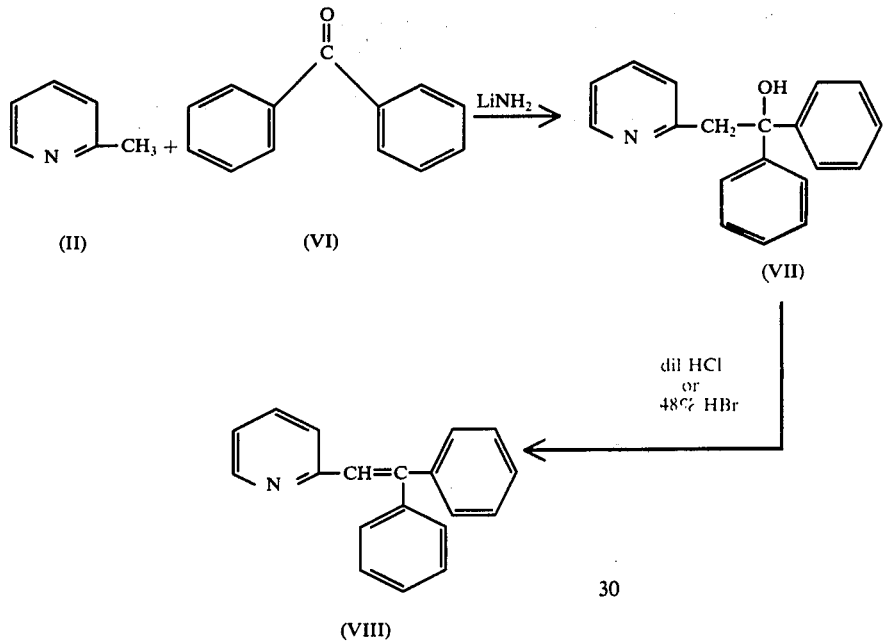

Previous attempts, however, to reduce the double bond, pyridine ring and the two phenyl rings of 2-(2,2-diphenylethenyl)pyridine (VIII) in a single step to obtain perhexiline (I) directly have heretofore been unreported.

SUMMARY OF INVENTION

In accordance with this invention, perhexiline (I) is directly prepared in a one-step process by the reduction of 2-(2,2-diphenylethenyl)pyridine (VIII). More particularly, the process of the present invention comprises reducing a mixture of 2-(2,2-diphenylethenyl)pyridine in a solvent selected from the group consisting of cyclohexane, pentane, hexane, heptane, dioxane or tetrahydrofuran using hydrogen at a pressure of from 70 to 140 atmospheres and at a temperature of from 160° to 250° C. in the presence of an anhydrous, finely-divided, porous Raney nickel catalyst. Not only does this process result in the reduction of the double bond and the pyridine ring as expected, but surprisingly results in the simultaneous reduction of both phenyl rings as well. This reaction can be schematically illustrated as follows:

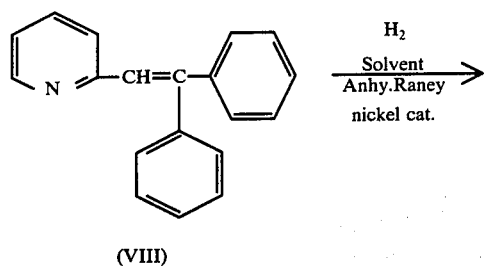

DETAILED DESCRIPTION OF THE INVENTION

Previously, the reduction of compounds analogous to 2-(2,2-diphenylethenyl) pyridine resulted only in a reduction of the heterocyclic portion of the molecule. Thus, Sury et al., Helv. Chim. Acta 2133, 2142 (1954) teach the selective reduction of 2-(diphenylmethyl)pyridine and related aromatic pyridines to the corresponding piperidines using either a platinum oxide catlyst or a Raney nickel catalyst. U.S. Pat. No. 3,252,982 describes the catalytic hydrogenation of 3-benzhydrylpiperidines. However, the simultaneous reduction of the double bond, pyridine ring and both phenyl rings has hithertofore been unreported.

Applicants have discovered a process whereby the compound 2-(2,2-diphenylethenyl)pyridine (VIII) can be completely reduced to perhexiline in a single step. The process of this invention provides a safe and economical method and is readily adapted to large scale batch or continuous production of perhexiline in yields greater than 90%. Moreover, when prepared in accordance with the preferred teachings of the present invention, perhexiline is obtained in high purity and in yields as high as 99.9%.

The starting material 2-(2,2-diphenylethenyl)pyridine (VIII) is readily prepared by the condensation of α-picoline and benzophenone in the presence of lithium amide to form α,α-diphenyl-2-pyridineethanol as illustrated in Example 1. Dehydration by means of phosphoric acid (85%), hydrobromic acid (48%) or hydrochloric acid to prepare 2-(2,2-diphenylethenyl)pyridine is illustrated in Example 2. Alternatively, the pyridineethanol compound may be dehydrated in situ, as illustrated in Example 3, this being a preferred route in the large scale production of perhexiline.

The reduction of 2-(2,2-diphenylethenyl)pyridine takes place in an atmosphere of hydrogen gas in a suitable reduction solvent. Solvents which are suitable in carrying out the reduction include cyclohexane, pentane, hexane, heptane, dioxane or tetrahydrofuran with cyclohexane being the solvent of choice.

The preparation of the anhydrous Raney nickel catalyst is critical with respect to obtaining a complete reduction of the 2-(2,2-diphenylethenyl)pyridine. Inadequate preparation of the catalyst results in a mixture of partially reduced compounds in which either the double bond and/or the pyridine ring and/or one of the phenyl rings is reduced with little, if any, reduction to the desired product, perhexiline. Of particular importance is the preparation of an anhydrous Raney nickel catalyst from which all traces of water have been removed. This is not to say that the treated catalyst is devoid of all water in an absolute sense, since there undoubtedly remains a small, but finite, amount of moisture present in the catalyst. Rather, it is to say that great care must be taken as a practical matter to substantially remove all traces of water.

It should be noted that the anhydrous, finely-divided, porous Raney nickel catalyst prepared in accordance with this invention is extremely pyrophoric in nature, and any exposure of the catalyst to air or oxygen must be avoided. Once prepared, the catalyst can be kept wet in an anhydrous solvent. Spent catalyst can be safely handled as an aqueous-solvent slurry. Alternatively, spent active catalyst can be washed free of organic material, stored under water and inactivated by the addition of solid sodium hypochlorite with stirring to form a 5 percent sodium hypochlorite solution.

The anhydrous Raney nickel catalyst employed in the process of this invention is utilized as a finely-divided, porous material. The catalyst is initially prepared as a 50:50 alloy of nickel and aluminum utilizing a graphite crucible at a temperature of 1000° C. The molten alloy is cooled, crushed to approximately ¼ pieces in a jaw crusher and physically reduced to a finely-divided granular state in a ball mill equipped with ½ steel balls (200 mesh U.S. Sieve Series). A solution of 7–10% sodium hydroxide is added to partially leach the aluminum from the surface of these granules. The resulting catalyst contains approximately 90% nickel and 9% aluminum and has a total particle size distribution of approximately 25% in the zero to 20 micron range, 70% in the zero to 40 micron range, and 99% in the zero to 100 micron range. Alternatively, the actual preparation of these catalysts can be avoided if desired inasmuch as they are readily available from commercial sources (Davison Chemical Division, W. R. Grace and Company).

As previously indicated, it has been found necessary to remove all of the water from the Raney nickel catalyst in order to achieve complete reduction of the 2-(2,2-diphenylethenyl)pyridine. Ordinarily, Raney nickel catalysts are prepared or supplied commercially as aqueous slurries. Raney nickel is highly polar and traces of water adhere tightly to it. Generally, the prepared catalyst is washed three or four times with approximately five or six volumes of anhydrous methanol per washing. The catalyst is then left standing overnight under an additional two volumes of anhydrous methanol. Allowing the multi-washed catalyst to stand overnight under the final anhydrous methanol wash improves its water removal, but does not achieve total water removal.

In order for the successful operation of the catalyst it has been found necessary to remove the final traces of water by azeotropic distillation. Solvents such as benzene, toluene, cyclohexane, pentane, hexane and heptane can be employed. Cyclohexane is the dehydration solvent of choice, inasmuch as it is also the preferred solvent in which the reduction is conducted. The final methanol wash is removed from the catalyst by decantation and replaced with an equal volume of cyclohexane. Residual methanol is removed on distillation as the cyclohexane-methanol azeotrope (b.p. 54° C.), followed by removal of water as the cyclohexane-water azeotrope (b.p. 70° C.). When all of the methanol and water have been removed, the reflux temperature increases to the boiling point of cyclohexane (81° C.), and a single layer is observed in the Dean-Stark trap.

In commercial operation, the properly prepared anhydrous catalyst can be recycled for reasons of economy. Inasmuch as the catalyst is subject to gradual poisoning and fouling, its efficiency becomes retarded with continued usage. Therefore, in catalyst recycling operations, increased catalyst loadings are commonly employed.

The process of this invention requires relatively high hydrogen pressures in order for the reaction to be completed in a reasonable period of time. Hydrogen pressures can vary over a wide range of pressure from about 70 to 140 atmospheres. In general, the higher the hydrogen pressure, the faster the rate of reduction. Thus, at a reaction temperature of about 200° C., the reduction of an approximately one molar solution of 2-(2,2-diphenylvinyl)pyridine in cyclohexane is essentially complete in about 1.5 hours at a hydrogen pressure of 140 atmosphere, whereas the corresponding reduction requires approximately 2.5 hours for completion at a hydrogen pressure of 70 atmospheres.

The progress of the reduction is readily followed by observing the amount of hydrogen taken up by the reaction mixture. Theoretically, ten moles of hydrogen per mole of 2-(2,2-diphenylvinyl)pyridine are required for the reduction to go to completion. On large scale production batches, the main pressure gauge of the hydrogen source can be used to monitor the progress of the reduction. The reduction can be safely continued until no further hydrogen uptake is observed.

Another critical feature of this invention is the temperature at which the process of this invention is conducted. At temperatures of less than 160° C., no appreciable reduction to 2-(2,2-dicyclohexylethyl)piperidine occurs. Too high a temperature, on the other hand, results in a thermal degradation of the reaction mixture. Thus, the process of this invention is conducted within a temperature range of from about 160° to about 250° C., and preferably at a temperature of about 200° C. to 210° C. The particular choice of temperature selected is a function of both the hydrogen pressure and the reduction period. Thus, generally the higher the hydrogen pressure, the lower the required temperature for the reduction process, within the above limits.

In general, the process of this invention is conducted in a solvent as a batch-operated heterogeneous reduction. A slurry of the finely-divided, porous, anhydrous Raney nickel catalyst in a suitable solvent is added to an appropriate reactor or autoclave previously purged with nitrogen or some other inert gas. Suitable solvents include those solvents which are inert and in which 2-(2,2-diphenylethenyl)pyridine is at least slightly soluble. The 2-(2,2-diphenylethenyl)pyridine, is dissolved or suspended in one of the aforementioned reduction solvents and added to the reaction vessel. After purging with nitrogen gas, hydrogen gas is introduced into the system to the desired pressure and the reactor is stirred and heated to its operating temperature. Hydrogenation is continued for approximately 3 to 5 hours or until further hydrogen uptake ceases. The reaction mixture is cooled and the catalyst removed by filtration, being careful to keep the catalyst continually wet and not exposed to air. The desired product can be recovered from the filtrate in accordance with well-known procedures, as for example by extraction or via solvent removal techniques.

A preferred method for recovering perhexiline is as its maleate salt. This salt has the further advantage of being obtained from the reaction mixture in almost quantitative yields. Moreover, the maleate is the particular salt form in wich perhexiline is therapeutically administered. Following reduction, the anhydrous Raney nickel catalyst is removed, washed, and the combined filtrates are evaporated in vacuo. The perhexiline residue is dissolved in a crystallizing solvent such as acetone, methyl ethyl ketone or a lower alkanol having from 1 to 4 carbon atoms. Illustrative of such lower alkanols are methanol, ethanol, propanol, isopropanol, butanol, isobutanol and $t$-butanol. The preferred solvents for the recovery of perhexiline maleate in accordance with this process are acetone or isopropanol.

A solution of maleic acid is prepared using the same crystallizing solvent and warmed to about 40°–50° C. The maleic acid solution is rapidly added with efficient stirring to the solution of perhexiline, whereupon perhexiline maleate precipitates. The solution is cooled to a final temperature of 15°–20° C. The product is removed by filtration, washed with cold crystallizing solvent and is obtained in high yield of excellent purity having a m.p. of 186°–189° C. A final recrystallization from methanol yields pharmaceutical grade material having a m.p. of 189°–191° C. The recovery of perhexiline maleate via this acetone procedure is so efficient that it can be utilized as a means for quantitating the amount of perhexiline formed during reduction.

Another preferred embodiment of this invention employs the use of a fixed-bed or trickle bed reactor with anhydrous Raney nickel catalyst in a continuous process. In its physical form the reactant solution is fed into a fixed-bed or trickle-bed column packed with pelleted or granular catalyst and allowed to trickle through the catalyst bed. Hydrogen gas is passed through the catalyst bed either concurrently or counter-currently to the liquid flow. The reaction takes place between the dissolved gas and liquid reactant at the catalyst surface. The product which is continuously formed is collected and removed from the bottom of the catalyst bed. In addition to providing for continuous operation, such a system has the advantage of eliminating the necessity of separating the catalyst from the reaction product at the completion of the reaction. Multiple feed passes and recyclizations can be easily installed to increase the efficiency of the reduction. Simplicity and reduced production costs make this method highly desirable for large-scale commercial operation.

The following specific Examples more clearly illustrate the process of making and using this invention and set forth the best mode contemplated by the inventors for carrying out their invention. However, these illustrations are not to be construed as limiting the scope of the invention claimed.

EXAMPLE 1

$\alpha,\alpha$-Diphenyl-2-Pyridineethanol

Benzophenone, 32.4 kg (177.8 mole), $\alpha$-picoline, 33.1 kg (355.5 moles), and lithium amide, 4.54 kg (197.4 moles) are charged into a 30 gallon reactor arranged for reflux operation. The mixture is stirred, rapidly heated to 125° C. and maintained at this temperature. The rate of ammonia evolution will gradually increase and after about 3 to 4 hours of reaction time only occasional heating is required to maintain the desired temperature and a rapid evolution of ammonia. After about 5 hours, a vigorous surge of ammonia evolution is noted. Following the ammonia surge, external heating is continued and the reaction maintained at 125° C. for an additional 6 to 8 hours. The reaction mixture is cooled to 70°–80° C. and rapidly added to approximately 230 liters of water at 25° C. Stirring is continued for approximately 30 minutes and the solid removed by filtration. The filter cake is thoroughly washed with water and dried at 60°–70° C. yielding 42·6 kg of $\alpha,\alpha$-diphenyl-2-pyridineethanol having a m.p. of 147°–51° C.

EXAMPLE 2

2-(2,2-Diphenylethenyl)Pyridine

The compound $\alpha,\alpha$-diphenyl-2-pyridineethanol, 46.0 kg (167.1 mole) is added to a mixture of 44 liters of 37% hydrochloric acid and 44 liters of water. The reaction mixture is heated to its reflux temperature and maintained for one hour. Approximately 100 liters of water are added and the temperature of the reaction mixture adjusted to 25° C. On cooling, the hydrochloride salt separates as an oil. A cold solution of 19.4 kg of sodium hydroxide dissolved in 20 liters of water is added at such a rate as to maintain the temperature of the reaction mixture below 30° . The 2-(2,2-diphenylethenyl)-pyridine base first separates as an oil which solidifies upon continued stirring and cooling. Stirring at 25°–30° C. is continued for approximately one hour to insure complete solidification of the product. The crude 2-(2,2-diphenylethenyl) pyridine is removed by filtration and washed with water until the final washing is essentially neutral. Approximately 43.0 kg of crude product is obtained having a melting point of 113°–7° C. Recrystallization of the crude material from isopropyl alcohol results in approximately 36.5 kg of 2-(2,2-diphenylethenyl)pyridine having an m.p. of 117°–9° C.

EXAMPLE 3

2-(2,2-Diphenylethenyl)Pyridine Prepared in situ

Benzophenone, 32.4 kg (177.8 moles), $\alpha$-picoline, 33.1 kg (355.5 moles), and lithium amide, 4.54 kg (197.4 moles) are placed in the reactor equipped for refluxing operation. The mixture is stirred and rapidly heated to its reflux temperature (125°–30° C.). The reaction mixture is maintained at its reflux temperature for approximately 3 to 4 hours. Occasional external heating is applied to maintain a rapid evolution of ammonia. After about 5 hours from the start of the reaction, a vigorous surge of ammonia evolution occurs. Following the ammonia surge, external heating is continued and the reaction maintained at 125° C. for a total period of about 12 hours. The reaction mixture is cooled to 100° C. and slowly added to a solution of 67 liters of 37% hydrochloric acid and 27 liters of water. The reaction mixture is heated to its reflux temperature and maintained at that temperature for a period of one hour. Approximately 60 liters of water are added and the temperature of the reaction mixture adjusted to about 10° C. During the cooling period, the hydrochloride salt of 2-(2,2-diphenylethenyl)pyridine separates as an oil. To the stirred reaction mixture is added a cold (5° C.) solution of 35.4 kg of sodium hydroxide (885 moles) contained in 42 liters of water at such a rate as to maintain the temperature of the reaction mixture below 30° C. The 2-(2,2-diphenylethenyl) pyridine base first separates as an oil, which upon continued stirring and cooling solidifies. Stirring is continued for approximately one hour at 25°–30° C. to ensure complete solidification of the product. The crude 2-(2,2-diphenylethenyl)pyridine is removed by filtration and washed well with water to yield 40.8 kg of material having an m.p. 103°–13° C. The crude product is dissolved in isopropyl alcohol, filtered, concentrated to remove about 20% of the isopropyl alcohol, and gradually cooled to 5° C. The desired 2-(2,2-diphenylethenyl)pyridine is removed by filtration, washed with cold isopropyl alcohol to yield 34.1 kg. of product having an m.p. of 117°–119° C.

EXAMPLE 4

Preparation of Anhydrous Raney Nickel Catalyst

Approximately 300 grams of a 50% aqueous slurry of Raney nickel catalyst consisting of 90% nickel and 9% aluminum and havng a total particle size distribution of 25% at zero to 20 microns, 70% at zero to 40 microns and 99% at zero to 100 microns (Raney-28, Davison Chemical Division, W. R. Grace and Company) is placed in a three liter, three-necked flask equipped with a stirrer. The aqueous layer is decanted and the catalyst is washed four times with anhydrous methanol using 5 to 6 volumes of methanol with stirring per wash. After each wash, the methanol is removed by decantation. After the final wash, the catalyst is permitted to remain overnight under 5 to 6 volumes of methanol. The methanol is again removed by decantation and replaced with approximately one liter of cyclohexane. The flask is fitted with a reflux condenser and a Dean-Stark trap and the catalyst contained therein is azeotropically distilled. Methanol is removed as a cyclohexane-methanol azeotrope which boils at 54° C., whereas the remaining traces of moisture are removed as a cyclohexane - water azeotrope boiling at 69° C. The catalyst prepared in this fashion is stored under cyclohexane until ready to be used.

Following essentially the same procedure, but substituting benzene, toluene, pentane, hexane and heptane for the cyclohexane above results in the preparation of an anhydrous Raney nickel catalyst suitable for reduction. Prior to using the catalyst, however, these solvents are replaced with cyclohexane as the reducing solvent.

EXAMPLE 5

2-(2,2-Dicyclohexylethyl)Piperidine

To a nitrogen-purged one liter autoclave is added 20 grams of cyclohexane-wet, anhydrous Raney nickel catalyst under 100 ml. of cyclohexane, prepared in accordance with the preceeding Example. A slurry of 100 g. (0.39 mole) of 2-(2,2-diphenylethenyl)pyridine in 300 ml. of cyclohexane is charged to the autoclave and the autoclave again flushed with nitrogen. Hydrogen gas is introduced with stirring to a pressure of 69–70 atmospheres. The mixture is heated to a temperature of about 200° C. Hydrogenation is continued at this temperature until hydrogen uptake ceases, usually a period of about 3 to 4 hours. The stirred reaction mixture is cooled to approximately 40° C., the autoclave vented and flushed with nitrogen to remove hydrogen. The catalyst is removed by filtration and washed with cyclohexane, care being taken to keep the catalyst wet at all times. The filtered catalyst is stored under cyclohexane for subsequent recycling or deactivation. The resulting filtrate is evaporated in vacuo to yield 108.2 g. of the desired 2-(2,2-dicyclohexylethyl)piperidine. Gas chromatographic analysis of this material indicates a 99.2% purity.

Following essentially the same procedure and substituting pentane, hexane, heptane, dioxane or tetrahydrofuran for the cyclohexane above results in the preparation of 2-(2,2-dicylohexylethyl)piperidine having substantially the same purity, but in varying yields.

EXAMPLE 6

2-(2,2-Dicyclohexylethyl)Piperidine Maleate

The compound 2-(2,2-dicyclohexylethyl)piperidine, 108.2 g. (0.39 mole) prepared in accordance with the preceeding Example is dissolved in 550 ml. of acetone. The solution is stirred at ambient temperature and treated with a hot solution of 46.4 g. (0.4 mole) of maleic acid in 200 ml. of acetone. The 2-(2,2-dicyclohexylethyl)piperidine maleate begins to precipitate immediately upon adition of the maleic acid solution. The mixture is cooled to 5° C. and filtered. The desired product is washed with 100 ml. of acetone and yields 145 g. of 2-(2,2-dicyclohexylethyl)piperidine maleate having a melting point of 18°–9° C.

EXAMPLE 7

Attempted Preparation of 2-(2,2-Dicyclohexylethyl)Piperidine

Approximately 25 g. of the Raney nickel catalyst prepared in Example 4 is placed in a three liter, 3-necked flask equipped with a stirrer. The aqueous layer is decanted and the catalyst is washed four times with anhydrous tetrahydrofuran using 5 to 6 volumes of tetrahydrofuran with stirring per wash. After each wash, the tetrahydrofuran is removed by decantation. After the final wash, the catalyst is permitted to remain overnight under 5 to 6 volumes of tetrahydrofuran. The tetrahydrofuran is removed by decantation and replaced with approximately 0.1 liters of fresh anhydrous tetrahydrofuran.

This mixture is placed in a nitrogen-purged one liter autoclave and a slurry of 100 g. (0.39 mole) of 2-(2,2-diphenylethenyl)pyridine in 300 ml. of tetrahydrofuran is charged to the autoclave. The autoclave is flushed with nitrogen and hydrogen gas is introduced with stirring to a pressure of 69–70 atmospheres. The mixture is heated to a temperature of about 200° C. Hydrogenation is continued at this temperature until hydrogen uptake ceases, usually a period of from about 3 to 4 hours. The stirred reaction mixture is cooled to approximately 40° C., the autoclave vented and flushed with nitrogen to remove hydrogen. The catalyst is removed by filtration and washed with anhydrous tetrahydrofuran, care being taken to keep the catalyst wet at all times. The filtered catalyst is stored under tetrahydrofuran for subsequent deactivation. The resulting filtrate is evaporated in vacuo to yield a crude product which is 82% perhexiline.

Following essentially the same procedure but omitting the tetrahydrofuran washings, results in the formation of a crude product which is 69.8% perhexiline.

EXAMPLE 8

Effects of Temperature of Reduction

Following essentially the same procedure described in Example 5, the reduction was conducted at the following temperatures. The following table illustrates the effect of temperature upon product yield.

| (a) DPVP, kg. | Cyclohexane, ml. | (b) Raney Nickel Catalyst, gms.(wet) | Temp., ° C. | H$_2$, atm. | (c) Yield Product % | (d) Product Purity % |
|---|---|---|---|---|---|---|
| 100 | 400 | 22.5 | 180 | 69 | 58.9 | 37.8 |
| 100 | 400 | 22.5 | 200 | 69 | 94.8 | 99.2 |
| 200 | 400 | 45.0 | 200 | 69 | 91.6 | 99.5 |
| 100 | 400 | 22.5 | 220 | 69 | 94.8 | 98.5 |
| 100 | 450 | 22.5 | 240 | 69 | 85.0 | 89.7 |

(a) 2-(2,2-diphenylethenyl)pyridine
(b) Raney-28 (Davison Chemical Division, W. R. Grace and Company)
(c) determined as maleate salt
(d) as determined by gas chromatography on crude free base

We claim:

1. A process for the preparation of 2-(2,2-dicyclohexylethyl)piperidine which comprises azeotropically distilling a mixture of finely-divided, porous Raney catalyst in a solvent selected from the group consisting of cyclohexane, pentane hexane, heptane, dioxane or tetrahydrofuran so as to remove all traces of moisture; adding a mixture of 2-(2,2-diphenylethenyl)pyridine in said solvent to said catalyst mixture; reducing said 2-(2,2-diphenylethenyl)pyridine in the presence of hydrogen at a pressure of from 70 to 140 atmospheres and at a temperature of from 160° to 250° C. and recovering the 2-(2,2-dicyclohexylethyl)piperidine obtained therefrom.

2. A process according to claim 1 wherein the solvent is cyclohexane.

3. A process for the preparation of 2-(2,2-dicyclohexylethyl)piperidine comprising azeotropically distilling a mixture of finely-divided, porous Raney nickel catalyst in cyclohexane so as to remove all traces of moisture, adding a solution of 2-(2,2-diphenylethyl)pyridine in cyclohexane to said catalyst mixture, reducing said mixture with hydrogen at a pressure of from 68 to 72 atmospheres and a temperature of from 200° to 210° C. until hydrogen uptake ceases, filtering said catalyst to obtain a clear filtrate, evaporating said filtrate to a residue, dissolving said residue in a crystallizing solvent selected from the group consisting of acetone, methyl ethyl ketone and a lower alkanol having from 1 to 4 carbon atoms, adding a solution of maleic acid dissolved in said recrystallizing solvent and recovering the precipitated 2-(2,2-dicyclohexylethyl)piperidine maleate therefrom.

4. A process according to claim 3 wherein the crystallizing solvent is acetone.

5. A process according to claim 3 wherein the crystallizing solvent is isopropyl alcohol.

* * * * *

UNITED STATES PATENT AND TRADEMARK OFFICE
CERTIFICATE OF CORRECTION

PATENT NO. : 4,069,222
DATED : January 17, 1978
INVENTOR(S) : Stephen W. Horgan, Frank P. Palopoli and Edward J. Schwoegler It is certified that error appears in the above-identified patent and that said Letters Patent are hereby corrected as shown below:

Column 5, line 40 "1/4 pieces" should read "1/4" pieces";
Column 5, line 42 "1/2 steel balls" should read "1/2" steel balls"; Column 11, lines 30-31 "Raney catalyst" should read "Raney nickel catalyst"; Column 12, line 14 "diphenylethyl" should read "diphenylethenyl".

Signed and Sealed this

Sixteenth Day of May 1978

[SEAL]

Attest:

RUTH C. MASON
Attesting Officer

LUTRELLE F. PARKER
Acting Commissioner of Patents and Trademarks